(12) United States Patent
Hossainy (10) Patent No.: US 7,223,282 B1
(45) Date of Patent: May 29, 2007

(54) REMOTE ACTIVATION OF AN IMPLANTABLE DEVICE

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 170 days.

(21) Appl. No.: 09/966,421

(22) Filed: Sep. 27, 2001

(51) Int. Cl.
*A61F 2/06* (2006.01)

(52) U.S. Cl. ................................ 623/1.15

(58) Field of Classification Search ........... 606/108, 606/191, 192, 194, 195, 197, 198; 623/1.1–1.22, 623/1.42–1.43; 424/426, 450
See application file for complete search history.

(56) References Cited

U.S. PATENT DOCUMENTS

| | | | |
|---|---|---|---|
| 4,188,373 A | 2/1980 | Krezanoski | 424/78 |
| 4,329,383 A | 5/1982 | Joh | 428/36 |
| 4,733,665 A | 3/1988 | Palmaz | 128/343 |
| 4,800,882 A | 1/1989 | Gianturco | 128/343 |
| 4,882,168 A | 11/1989 | Casey et al. | 424/468 |
| 4,886,062 A | 12/1989 | Wiktor | 128/343 |
| 4,941,870 A | 7/1990 | Okada et al. | 600/36 |
| 4,977,901 A | 12/1990 | Ofstead | 128/772 |
| 5,112,457 A | 5/1992 | Marchant | 204/165 |
| 5,165,919 A | 11/1992 | Sasaki et al. | 424/488 |
| 5,272,012 A | 12/1993 | Opolski | 428/423.1 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,328,471 A | 7/1994 | Slepian | 604/101 |
| 5,330,768 A | 7/1994 | Park et al. | 424/501 |
| 5,380,299 A | 1/1995 | Fearnot et al. | 604/265 |
| 5,417,981 A | 5/1995 | Endo et al. | 424/486 |
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A | 11/1995 | Berg et al. | 427/2.3 |
| 5,569,463 A | 10/1996 | Helmus et al. | 424/426 |
| 5,573,934 A | 11/1996 | Hubbell et al. | 435/177 |
| 5,578,073 A | 11/1996 | Haimovich et al. | 623/1 |
| 5,605,696 A | 2/1997 | Eury et al. | 424/423 |
| 5,609,629 A * | 3/1997 | Fearnot et al. | 623/1.42 |

(Continued)

FOREIGN PATENT DOCUMENTS

EP 0 301 856 2/1989

(Continued)

OTHER PUBLICATIONS

Hirsch et al., *Metal Nanoshells as a Novel Substrate for Biosensing Applications*, Society for Biomaterials, Sixth World Congress Transactions, p. 153.

(Continued)

*Primary Examiner*—Michael J. Hayes
*Assistant Examiner*—Victor Nguyen
(74) *Attorney, Agent, or Firm*—Squire, Sanders & Dempsey L.L.P.

(57) ABSTRACT

The invention is directed to an implantable device, such as a stent, for delivering a therapeutic substance. The device includes a reservoir containing a therapeutic substance and an energy converter to cause the release of the substance.

54 Claims, 3 Drawing Sheets

U.S. PATENT DOCUMENTS

| | | | |
|---|---|---|---|
| 5,624,411 A | 4/1997 | Tuch | 604/265 |
| 5,628,730 A | 5/1997 | Shapland et al. | 604/21 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,716,981 A | 2/1998 | Hunter et al. | 514/449 |
| 5,735,897 A | 4/1998 | Buirge | 623/12 |
| 5,746,998 A | 5/1998 | Torchilin et al. | 424/9.4 |
| 5,776,184 A | 7/1998 | Tuch | 623/1 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,925,720 A | 7/1999 | Kataoka et al. | 525/523 |
| 5,955,509 A | 9/1999 | Webber et al. | 514/772.7 |
| 5,964,744 A | 10/1999 | Balbierz et al. | 604/530 |
| 5,971,954 A | 10/1999 | Conway et al. | 604/96 |
| 5,972,029 A | 10/1999 | Fuisz | 623/1 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,026,316 A * | 2/2000 | Kucharczyk et al. | 600/420 |
| 6,033,582 A | 3/2000 | Lee et al. | 216/37 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,071,944 A | 6/2000 | Rodgers et al. | |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,187,037 B1 | 2/2001 | Satz | |
| 6,200,307 B1 | 3/2001 | Kasinkas et al. | |
| 6,201,065 B1 | 3/2001 | Pathak et al. | 525/90 |
| 6,203,551 B1 | 3/2001 | Wu | 606/108 |
| 6,231,600 B1 | 5/2001 | Zhong | 623/1.42 |
| 6,237,398 B1 * | 5/2001 | Porat et al. | 73/54.09 |
| 6,240,616 B1 * | 6/2001 | Yan | 29/527.2 |
| 6,241,719 B1 | 6/2001 | Wallace et al. | |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,254,634 B1 * | 7/2001 | Anderson et al. | 623/1.42 |
| 6,258,121 B1 | 7/2001 | Yang et al. | 623/1.46 |
| 6,273,908 B1 * | 8/2001 | Ndondo-Lay | 623/1.43 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,176 B1 | 10/2001 | Whitbourne | 623/23.59 |
| 6,312,457 B1 * | 11/2001 | DiMatteo et al. | 623/1.13 |
| 6,331,313 B1 | 12/2001 | Wong et al. | 424/427 |
| 6,335,029 B1 | 1/2002 | Kamath et al. | 424/423 |
| 6,346,110 B2 | 2/2002 | Wu | 606/108 |
| 6,352,683 B1 * | 3/2002 | ten Cate | 424/9.34 |
| 6,358,556 B1 | 3/2002 | Ding et al. | 427/2.24 |
| 6,379,380 B1 | 4/2002 | Satz | |
| 6,379,381 B1 | 4/2002 | Hossainy et al. | 623/1.42 |
| 6,383,217 B1 | 5/2002 | Satz | |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,475,644 B1 | 11/2002 | Hampikian et al. | |
| 6,494,862 B1 | 12/2002 | Ray et al. | 604/96.01 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,520,957 B1 | 2/2003 | Kasinkas et al. | |
| 6,527,801 B1 | 3/2003 | Dutta | 623/1.46 |
| 6,527,863 B1 | 3/2003 | Pacetti et al. | 118/500 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,569,688 B2 * | 5/2003 | Sivan et al. | 436/518 |
| 6,572,644 B1 | 6/2003 | Moein | 623/1.11 |
| 6,579,847 B1 * | 6/2003 | Unger | 514/2 |
| 6,585,765 B1 | 7/2003 | Hossainy et al. | 623/1.45 |
| 6,585,926 B1 | 7/2003 | Mirzaee | 264/400 |
| 6,605,154 B1 | 8/2003 | Villareal | 118/500 |
| 6,725,081 B2 | 4/2004 | Ciezki et al. | |
| 6,736,842 B2 | 5/2004 | Healy et al. | |
| 6,758,859 B1 * | 7/2004 | Dang et al. | 623/1.15 |
| 6,764,507 B2 * | 7/2004 | Shanley et al. | 623/1.16 |
| 6,776,792 B1 | 8/2004 | Yan et al. | |
| 6,783,543 B2 * | 8/2004 | Jang | 623/1.15 |
| 6,887,862 B2 | 5/2005 | Rychnovsky | |
| 6,899,723 B2 | 5/2005 | Chen | |
| 6,939,376 B2 | 9/2005 | Shulze et al. | |
| 2001/0018469 A1 | 8/2001 | Chen et al. | 523/121 |
| 2001/0037145 A1 | 11/2001 | Guruwaiya et al. | 623/1.15 |
| 2002/0077693 A1 | 6/2002 | Barclay et al. | 623/1.13 |
| 2002/0091433 A1 | 7/2002 | Ding et al. | 623/1.2 |
| 2002/0095197 A1 | 7/2002 | Lardo et al. | |
| 2002/0155212 A1 | 10/2002 | Hossainy | 427/2.25 |
| 2003/0065377 A1 | 4/2003 | Davila et al. | 623/1.13 |
| 2003/0099712 A1 | 5/2003 | Jayaraman | 424/486 |
| 2004/0202692 A1 | 10/2004 | Shanley et al. | |
| 2005/0158363 A1 | 7/2005 | Shalaby | |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |

| | | |
|---|---|---|
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15694 | 3/2001 |
| WO | WO 01/15751 | 3/2001 |
| WO | WO 01/17577 | 3/2001 |
| WO | WO 01/35997 | 5/2001 |
| WO | WO 01/45763 | 6/2001 |
| WO | WO 01/49338 | 7/2001 |
| WO | WO 01/74414 | 10/2001 |
| WO | WO 02/03890 | 1/2002 |
| WO | WO 02/026162 | 4/2002 |
| WO | WO 02/34311 | 5/2002 |
| WO | WO 02/056790 | 7/2002 |
| WO | WO 02/096365 | 12/2002 |
| WO | WO 02/100326 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Nov. 6, 1997 *Light Emitting Diodes Technology*, http://www.spacelink.msfc.nasa.gov/NASA . . . /97-11-06.Light.Emitting.Diodes.Technolog, printed Feb. 28, 2003 (3 pages).

Anonymous, *Cardiologist Draw—Up The Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96 (1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

*First Brain Cancer Surgeries Using New Space-Age Probe Are Successful*, Marshall Space Flight Center News Release, Sep. 30, 1999, http://www.msfc.nasa.gov/news/news/releases/1999/99-252.html, printed Feb. 28, 2003 (4 pages).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

*Light being used to fight cancer, NASA technology helps treat brain tumors*, http://www.cnn.com/TECH/science/9810/01/t_t/katie.brain/index.html, printed Feb. 28, 2003 (3 pages).

*Light Emitting Diodes Aid in Wound Healing*, http://healthlink.mcw.edu/content/printer-friendly/article_printer_friendly?975450257, printed Feb. 28, 2003 (3 pages).

*Light-Emitting Diodes*, http://www.mcw.edu/whelan/html/6, printed Feb. 28, 2003 (2 pages).

Liu et al., *Drug release characteristics of unimolecular polymeric micelles*, Journal of Controlled Release 68:167-174 (2000).

Marconi et al., *Covalent bonding of heparin to vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6):2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

*SCVIR Meeting: Light-Activated Drug Shrinks Plaque Build-up In Arteries*, Doctor's Guide, Mar. 23, 1999 file://. . .\A SCVIR MEETING Light-Activated Drug Shrinks Plaque Build-up In Arteries.ht, printed May 17, 2001(2 pages).

Shigeno, *Prevention of Cerebrovascular Spasm By Bosentan, Novel Endothelin Receptor*, Chemical Abstract 125:212307 (1996).

Turke, *Life-Emitting Diodes: LEDs Promote Healing*, Medical Product Manufacturing News (Mar. 2001). http://www.devicelink.com/grabber.php3?URL=http://www.devicelink.com/mpmn/arch . . . /0103mp006.htm, printed Mar. 3, 2003.

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

Oh et al., *Research on annihilation of cancer cells by glass-ceramics for cancer treatment with external magnetic field. I. Preparation and cytotoxicity*, J Biomed Mater Res 54:360-365, 2001.

Shershen et al., *Temperature-Sensitive Polymer-Nanoshell Composites for Modulated Drug Delivery Applications*, Society for Biomaterials, Sixth World Congress Transactions.

* cited by examiner

REMOTE ACTIVATION OF AN IMPLANTABLE DEVICE

BACKGROUND OF THE INVENTION

1. Field of the Invention

This invention relates generally to implantable devices, such as expandable intraluminal prosthesis. More particularly, this invention relates to a stent that delivers a therapeutic substance. Moreover, the present invention relates to a method of delivering a therapeutic substance with a stent.

2. Description of the Background

A variety of surgical procedures and medical devices are currently used to relieve intraluminal constrictions caused by disease or tissue trauma. An example of one such procedure is percutaneous transluminal coronary angioplasty (PTCA). PTCA is a catheter-based technique whereby a balloon catheter is inserted into a blocked or narrowed coronary lumen of the patient. Once the balloon is positioned at the blocked lumen or target site, the balloon is inflated causing the remodeling of the lumen. The catheter is then removed from the target site thereby allowing blood to freely flow through the lumen.

Although PTCA and related procedures aid in alleviating intraluminal constrictions, such constrictions or blockages reoccur in many cases. The cause of these recurring obstructions, termed restenosis, is due to the body's immune system responding to the trauma of the surgical procedure. As a result, the PTCA procedure may need to be repeated to repair the damaged lumen.

Stents or drug therapies, either alone or in combination with the PTCA procedure, are often used to avoid or mitigate the effects of restenosis at the surgical site. In general, stents are small, cylindrical devices whose structure serves to create or maintain an unobstructed opening within a lumen. The stents are typically made of, for example, stainless steel, Nitinol or other materials and are delivered to the target site via a balloon catheter. Although stents are effective in opening the stenotic lumen, the foreign material and structure of the stents themselves may exacerbate the occurrence of restenosis or thrombosis.

Drugs or therapeutic agents that limit migration and/or proliferation of vascular smooth muscle cells are used to significantly reduce the incidence of restenosis and thrombosis. Examples of various therapeutic agents commonly used include heparin, antithrombogenic agents, steroids, ibuprofen, antimicrobials, antibiotics, antiproliferatives, tissue plasma activator inhibitors, monoclonal antibodies, anti-inflammatory substances, and antifibrosis agents.

Should the therapeutic agents be applied systemically to the patient, they are absorbed not only by the tissues at the target site, but by all areas of the body. As such, one drawback associated with the systemic application of drugs is that areas of the body not needing treatment are also affected. To provide a more site-specific treatment, stents are frequently used as a means of delivering the drugs exclusively to the target site. The drugs are included or incorporated in a tissue-compatible polymer, such as a silicone, polyurethane, polyester, hydrogel, hyaluronate, and various copolymers and blended mixtures thereof. By positioning the stent at the target site, the drugs can be applied directly to the area of the lumen requiring therapy.

The above-described device, for treatment of restenosis and thrombosis, offers many advantages to potential patients. However, such devices may be deficient in their current drug-delivery capabilities. In particular, restenosis does not necessarily develop at a constant rate. The polymer-coated device may have limited effectiveness because the therapeutic agents are released by passive diffusion, and therefore do not have a release pattern that corresponds to the pathological cascade of restenosis.

In view of the above, it is apparent that there is a need to provide a drug delivery device which can control the release of the therapeutic agents so that conditions such as restenosis, that develop at a variable rate, can be more effectively treated.

SUMMARY OF THE INVENTION

Herein is described an implantable device, such as a stent, for delivering a therapeutic substance comprising a first material carried by the stent containing a therapeutic substance, and a second material carried by the stent to convert a first type of energy received by the second material from an energy source positioned external to the body vessel to a second type of energy, wherein the second type of energy promotes release of the therapeutic substance from the first material.

In an embodiment of the present invention, the second material can be, for example, Au, an Au-alloy, or ferrimagnetic glass-ceramic. In one variation, the second material can be Au particles with average diameters of, for example, from about 100-350 nm. In one embodiment, the second material can be capable of converting electromagnetic waves into thermal energy.

In one embodiment of the present invention, the first material is a temperature-sensitive hydrogel. The temperature-sensitive hydrogel can be N-isopropylacrylamide, polyoxyethylene-polyoxypropylene block copolymers, poly (acrylic acid) grafted pluronic copolymers, chitosan grafted pluronic copolymer, elastin mimetic polypeptides, and combinations and mixtures thereof.

Herein is also disclosed a method of delivering a therapeutic substance from a stent comprising inserting into a body vessel a stent comprising a first material containing a therapeutic substance and a second material capable of converting a first type of energy to a second type of energy, and applying to the second material a first type of energy from an energy source external to the body vessel wherein the second material converts the first type of energy to the second type of energy and the second type of energy promotes the release of the therapeutic substance from the first material.

Herein is also disclosed a stent for delivering thermal energy to a body vessel comprising a tubular body for implanting in a body vessel, and an energy converter carried by the tubular body to convert a first type of energy into thermal energy, wherein the energy converter is positioned to release the thermal energy to tissues adjacent to the tubular body and is responsive to an energy source remote from and not in direct physical contact with the energy converter.

Herein is also described a system for delivering a therapeutic substance comprising a device for implanting in the body, a reservoir carried by the device containing a therapeutic substance, an energy converter carried by the device to convert a first type of energy to a second type of energy to release the therapeutic substance from the reservoir, and an energy emitter for emitting the first type of energy to the energy converter.

DETAILED DESCRIPTION

Figure 1:
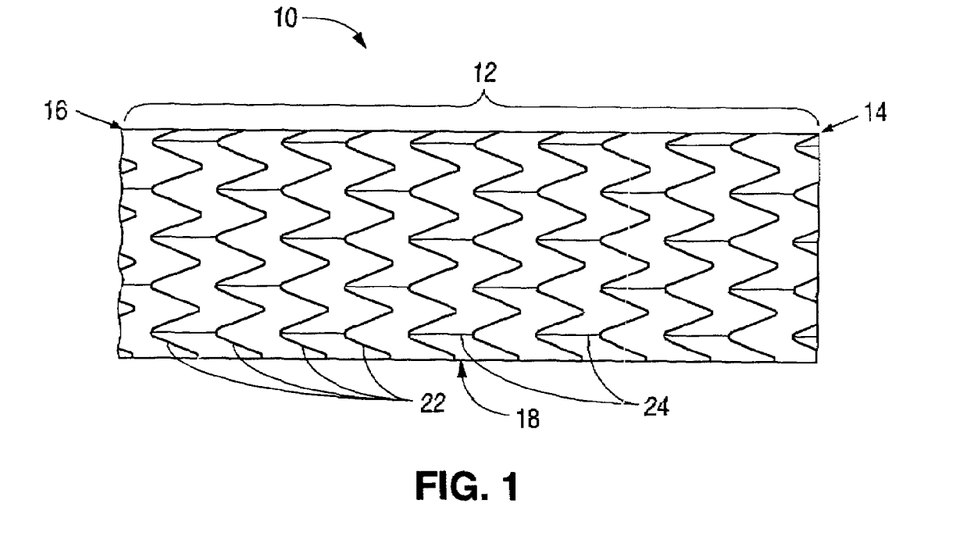
FIG. 1 is a side-view of a conventional stent in accordance with an embodiment of the present invention.

FIG. 1 illustrates an implantable prosthetic medical device. In the spirit of convenience and brevity, the medical device referenced in the text and figures of the present invention is a stent 10. However, it should be noted that other medical devices or prosthesis are also within the scope of the claimed invention. Suitable examples of other devices can include grafts (e.g., aortic grafts), stent-grafts, artificial heart valves, cerebrospinal fluid shunts, pacemaker electrodes, axius coronary shunts, and endocardial leads (e.g., FINELINE® and ENDOTAK®, available from Guidant Corporation).

Figure 2:
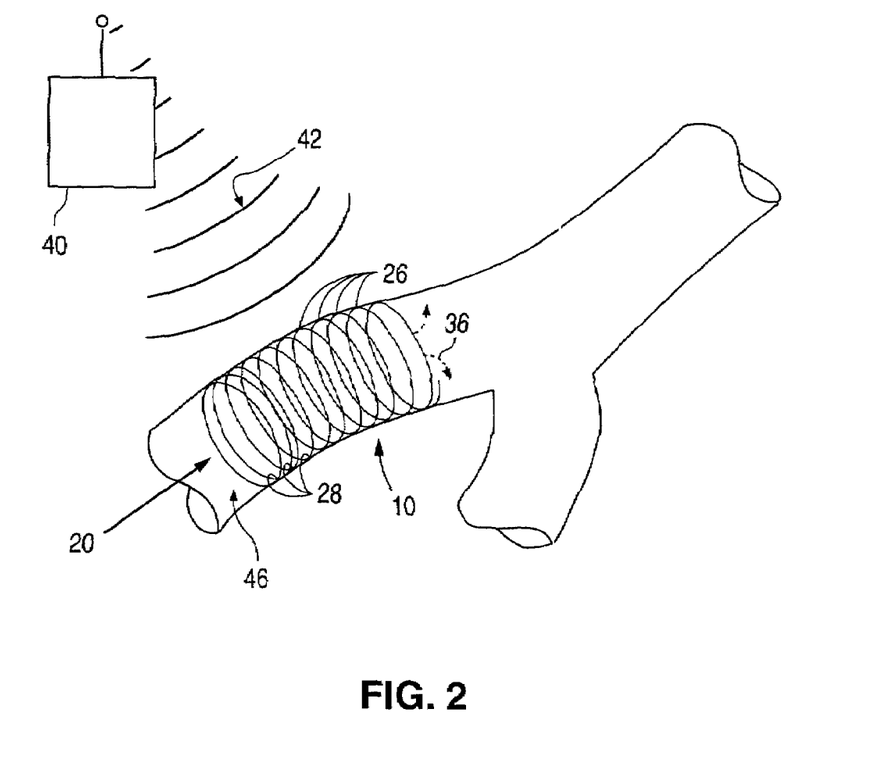
FIG. 2 is a diagram of an embodiment of the remote delivery system including a stent inserted into a body vessel.

As shown in FIGS. 1 and 2, stent 10 can have a tubular body structure 12, including a first end 14, a second end 16, and a mid-section 18. The structure of stent 10 should allow stent 10 to be inserted into and physically uphold an anatomical passageway by exerting a radially outward-extending force against the walls or inner lumen surface of the passageway. If desired, stent 10 can also expand the opening of the lumen to a diameter greater than its original diameter and, thereby, increase fluid flow through the lumen.

Stent 10 can include struts 22 that form a network structure. Struts 22 are radially expandable and interconnected by connecting elements 24 that are disposed between adjacent struts 22. Both struts 22 and connecting elements 24 have an outer (or lumen contacting) surface 26 and an inner surface 28, as shown in FIG. 2. In addition, a hollow bore 20 extends longitudinally through body structure 12 of stent 10.

Figure 3:
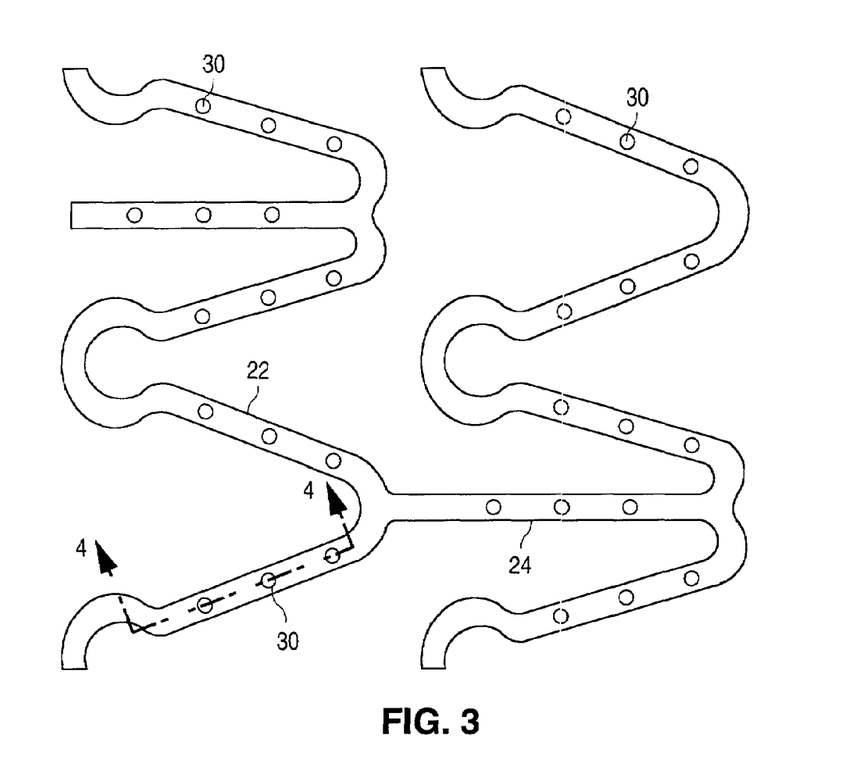
FIG. 3 illustrates an enlarged view of a portion of a stent.
Figure 4:
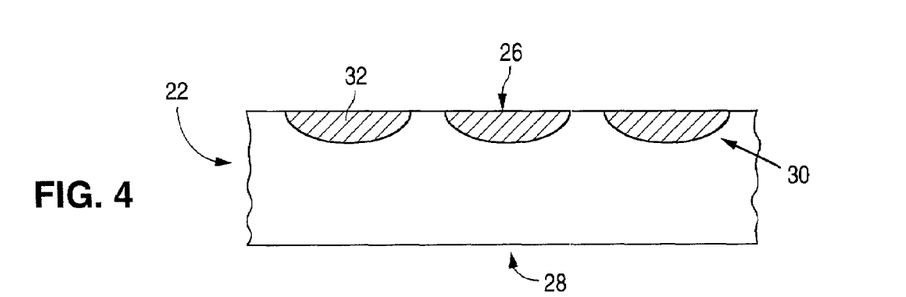
FIG. 4 illustrates a partial cross-section of a strut along the line 4-4 of FIG. 3.

Referring to FIG. 3, one or more depots (e.g., microdepots) or pores 30 can be formed on the surface of struts 22 and/or connecting elements 24. These depots 30 can act as reservoirs for various substances. In one embodiment of the present invention, as shown in FIG. 4, depots 30 that are formed on outer surface 26 carry an energy conversion material 32. Energy conversion material 32 can be any material that is capable of receiving a stimuli and converting such a stimuli to a form of energy. In one embodiment, for example, energy conversion material 32 is able to convert a first type of energy (e.g., electromagnetic, thermal, chemical) into a second type of energy (e.g., electromagnetic, thermal, chemical).

In one embodiment, gold (Au), in the form of particles, can be used as energy conversion material 32. The Au particles can be contained in depots 30 by various means, including but not limited to, by polymeric adhesives, or by sintering the Au particles in depots 30.

If the Au particles are exposed to electromagnetic waves, for example, the Au particles can convert the electromagnetic energy into thermal energy. The Au particles can have, for example, an average diameter from about 100-350 nm. The Au particles can have a silica nanoparticle core (e.g., 100-250 nm diameter) encapsulated by a thin (e.g., 1-100 nm) gold shell. By changing the relative thickness of the particle's core and shell, one can choose the peak absorbance to anywhere from about 600 nm to about 1400 nm. Au particles of this type can be capable of converting non-cytotoxic electromagnetic waves with wavelengths between 800 nm and 1200 nm into thermal energy. With the use of non-cytotoxic electromagnetic waves as the first energy type, the body tissues surrounding the body vessel do not readily absorb or refract the waves.

Since the Au particles are carried by depots 30 which are disposed on outer surface 26 as shown in FIG. 4, if inserted into a blood vessel, the stent can deliver heat to the tissues surrounding the blood vessel and cause heat shock protein generation. As a result, it is believed that restenosis in the blood vessel can be reduced.

One of ordinary skill in the art will understand that energy conversion materials 32 besides Au particles are within the scope of the invention. For instance, ferrimagnetic glass-ceramics can be used as energy conversion material 32. These ferrimagnetic glass-ceramics can convert magnetic field energy to thermal energy. A representative of this type of material is the ferrimagnetic glass-ceramics containing lithium ferrite and hematite crystallites in the system $Al_2O_3$—$SiO_2$—$P_2O_5$. Also, one of ordinary skill in the art will understand that various parameters can be altered in order to control the thermal output of energy conversion material 32 such as core-shell ratio, the wavelength applied to the energy conversion material 32, the intensity of the radiation and the use of an insulating material.

Figure 5:
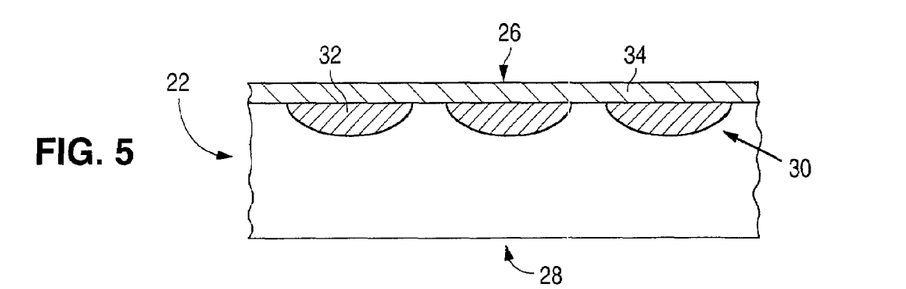
FIG. 5 illustrates the partial cross-section of the strut in accordance with one embodiment of the invention.

As shown in FIG. 5, a carrier material 34 can coat at least a portion of outer surface 26 for release of a therapeutic substance in response to the stimuli. In one embodiment, carrier material 34 can be a temperature-sensitive hydrogel. "Hydrogel" is intended to include a cross-linked polymer, via covalent, ionic, or hydrogen bonding, to form a three-dimensional open lattice structure which is capable of entrapping water molecules to form a gel.

Figure 6:
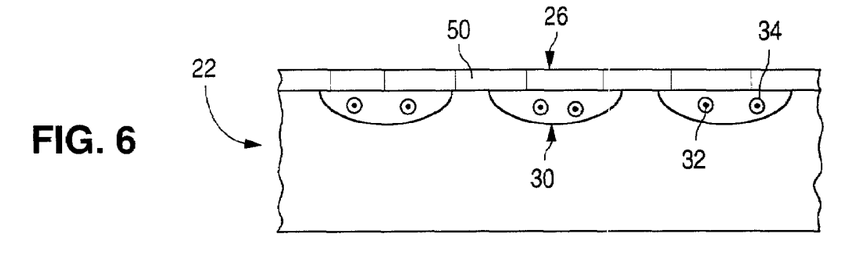
FIG. 6 illustrates the partial cross-section of the strut in accordance with another embodiment of the invention.

In another embodiment, as shown in FIG. 6, the hydrogel can be in the form of particles, microparticles, spheres, or ovoids. Particles, microparticles, spheres, or ovoids of the hydrogel can be formed by, for example, extrusion with a non-miscible substance such as oil, e.g., mineral oil or by agitation of the aqueous phase in contact with a non-miscible phase such as an oil phase to form small droplets. The macromer is then polymerized such as by exposure to light irradiation or to heat. Inclusion of a therapeutic substance mixed with the aqueous macromer solution results in the encapsulation of the therapeutic substance in the hydrogel. Energy conversion material 32 (e.g., Au particles) may also be encapsulated in the small droplets of the hydrogel.

For purposes of this invention, "temperature-sensitive hydrogel" means a hydrogel whose matrix constricts or collapses by exposing the hydrogel to a temperature greater than the hydrogel's lower critical solution temperature (LCST). The LCST (i.e., the temperature at which constriction occurs), should be above 37° C. (i.e., average human body temperature). One suitable example of a temperature-sensitive hydrogel is N-isopropylacrylamide (NIPAAm). One of ordinary skill in the art can also appreciate the implementation of other hydrogels in the polymeric coating of the present invention. Representative examples include polyoxyethylene-polyoxypropylene block copolymers (e.g., PLURONIC®, BASF Corporation, Parsippany, N.J.) such as those described in U.S. Pat. No. 4,188,373; poly(acrylic acid) or chitosan (a deacylated derivative of chitin) grafted pluronic copolymers, in which the grafted poly(acrylic acid) or chitosan improve the bio-adhesive properties of the hydrogel; and combinations and mixtures thereof, as well as elastin mimetic polypeptides, which are protein polymers based on the pentameric repeat-[(Val/Ile)-Pro-Gly-Xaa-Gly]$_5$-, where Xaa is an amino acid and is Val in the first four repeat units and Ile or Lys for the last repeat. With Xaa of Ile in the last repeat unit and a pH of 7, the elastin-mimetic polypeptide has a transition temperature of approximately 37° C.

Referring to FIG. 2, energy conversion material 32 (e.g., Au particles) (not shown) can receive at least a portion of electromagnetic waves 42 emitted by an energy emitter 40 that is positioned external to body vessel 46 or completely external to the body of the patient. The Au particles are able to absorb electromagnetic waves 42 and convert the electromagnetic energy into thermal energy which is released into the environment adjacent to the Au particles. Should stent 10 be coated with a hydrogel containing a therapeutic substance, the thermal energy or stimuli can be used to promote the release of the therapeutic substance. For example, once the temperature surrounding the hydrogel exceeds the hydrogel's transition temperature, the hydrogel contracts. As the hydrogel contracts, it elutes the therapeutic substance by "squeezing" the substance out of the hydrogel's matrix. As shown in FIG. 2, therapeutic substance 36 is thereby locally delivered to body vessel 46. In order to reduce the amount of therapeutic substance 36 eluted into the aqueous environment before remote activation, it would be useful to pair an anionic hydrogel with a cationic therapeutic substance.

The therapeutic substance can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the therapeutic substance can be for enhancing wound healing in a vascular site or improving the structural and elastic properties of the vascular site. Examples of substances include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin I$_1$, actinomycin X$_1$, and actinomycin C$_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. The foregoing substances are listed by way of example and are not meant to be limiting. Other therapeutic substances which are currently available or that may be developed in the future are equally applicable.

Referring to FIG. 6, in another embodiment, carrier material 34 (e.g., temperature-sensitive hydrogel), in the form of ovoids, encapsulates energy conversion material 32. Carrier material 34 further includes a therapeutic substance. As shown in FIG. 6, carrier material 34 is carried by depots 30, and is covered by a topcoat 50. In one embodiment, topcoat 50 is a hydrophilic polymer that inhibits the diffusion of the therapeutic substance from carrier material 34 until energy conversion material 32 is activated. A representative example of topcoat 50 is a blend of polyethylene glycol (PEG) and bishydroxyethoxypropylpolydimethylsiloxane (PDMS).

Figure 7:
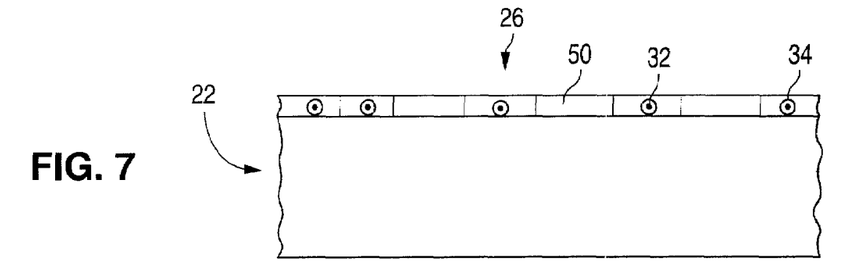
FIG. 7 illustrates the partial cross-section of the strut in accordance with another embodiment of the invention.

Referring to FIG. 7, in an alternative embodiment, carrier material 34, including energy conversion material 32 and a therapeutic substance, is suspended in topcoat 50. In one embodiment, topcoat 50 is a hydrophilic polymer that inhibits the diffusion of the therapeutic substance from carrier material 34 until energy conversion material 32 is activated.

Figure 8:
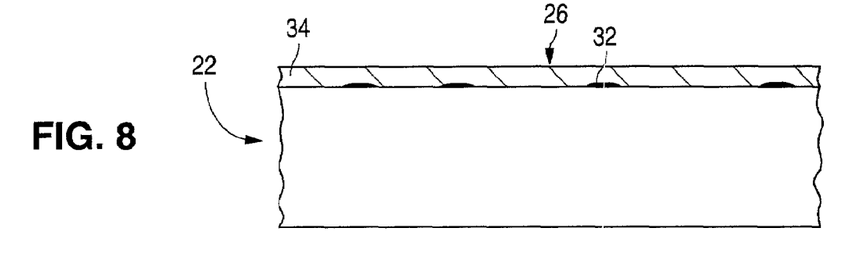
FIG. 8 illustrates the partial cross-section of the strut in accordance with another embodiment of the invention.

Referring to FIG. 8, in a further embodiment, instead of being carried by depots 30, energy conversion material 32 (e.g., Au particles) can be attached directly to outer surface 26 of stent 10 over which carrier material 34 (e.g., a hydrogel coating) is deposited. Energy conversion material 32 can be in the form of particles randomly disbursed or evenly distributed on outer surface 26. Alternatively, the density of energy conversion material 32 could be greater at each end 14 and 16 of stent 10 compared to mid-section 18 of stent 10. One of ordinary skill in the art will understand that the location and configuration of energy conversion material 32, and its position relative to carrier material 34, may vary according to clinical purpose and usage requirements and the particular type of stent 10 used to carry the components.

Figure 9:
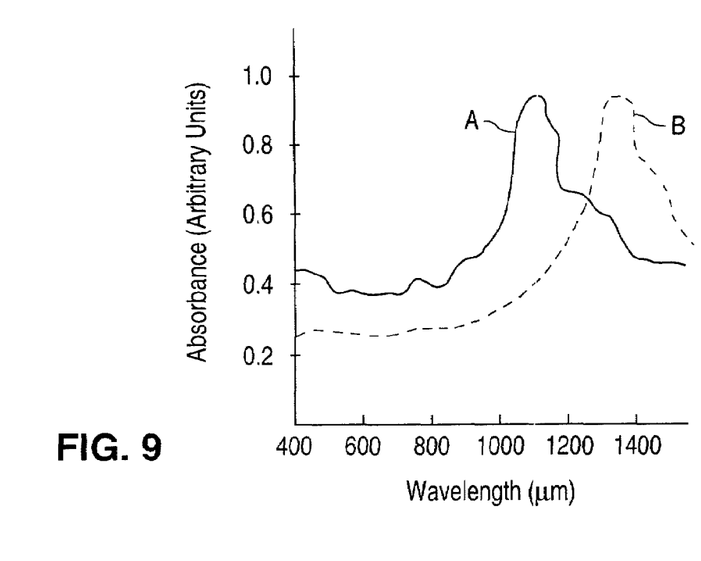
FIG. 9 graphically illustrates absorbance spectra of Au particles.

Alternatively, two or more different types of energy conversion materials can be used. For example, depots 30 at ends 14, 16 of stent 10 can carry Au particles, whereas depots 30 at mid-section 18 carry an Au—Cu alloy. By providing stent 10 with different types of energy conversion material 32, there can be a non-uniform response to energy emitted so that the delivery of the therapeutic substance can differ either spatially, or temporally. For example, in the case of Au particles, particles with different core-shell ratios will have different peak absorbance profiles. Referring to FIG. 9, the absorbance spectra for particles A and B show that particle A has a different peak absorbance than particle B. By matching particle A with a carrier material that carries a different therapeutic substance than that matched with particle B, different therapeutic substances can be delivered at different wavelengths.

The present invention also includes a method of delivering a therapeutic substance from a stent in a body vessel. Again referring to FIG. 2, in one embodiment, stent 10 is inserted into body vessel 46 and then electromagnetic waves 42 are applied by using energy emitter 40 that is positioned external to body vessel 46. Stent 10 may comprise Au particles and a temperature-sensitive hydrogel that encapsulates a therapeutic substance. The Au particles are able to absorb the electromagnetic waves 42 and convert the electromagnetic energy into thermal energy which is transferred to the temperature-sensitive hydrogel. In one embodiment, the Au particles have an average diameter from about 100-350 nm. In another embodiment, the electromagnetic waves can have a wavelength of between 800 and 1200 nm. Once the environmental temperature surrounding the hydrogel reaches the hydrogel's transition temperature, the hydrogel contracts. As the hydrogel contracts, the hydrogel elutes the therapeutic substance by "squeezing" the therapeutic substance out of the hydrogel's matrix. As shown in FIG. 2, therapeutic substance 36 is locally delivered to body vessel 46.

EXAMPLES

The following prophetic examples are given by way of illustration.

Example 1

Stents are cleaned with isopropyl alcohol in combination with ultrasonication. Au particles are mixed with a macromer solution and become suspended at a concentration of 30% w/w. The macromer solution contains 15% diacrylate end-capped pluronic diacrylate, 2.5% ethylene glycol dimethacrylate (EGDMA) (all monomer percentages are in molar), 0.5% benzolyl peroxide, 5% polyvinyl pyrrolidone (PVP), 7% ReoPro®(Eli Lilly and Company, Indianapolis, Ind.), and 70% $H_2O$. The Au suspension solution is applied as a coating to the surface of the stents with a wet weight of 1000 μg. The coating is heated at 65° C. for 4 minutes to induce a cross-linking reaction. Following the cross-linking reaction, the coating is dried in a vacuum oven at 40° C. for 12 hr. Then the macromer solution (without Au particles) is applied to the surface of the stents by dip-coating with a wet weight of 800 μg. The coating is heated at 65° C. for 4 minutes to induce a cross-linking reaction. Following the cross-linking reaction, the coating is dried in a vacuum oven at 40° C. for 12 hr. The coating is activated by directing a 900-1200 nm wavelength light in the infrared region of the electromagnetic spectrum to the coating.

Example 2

Stents are cleaned with isopropyl alcohol in combination with ultrasonication. Au particles are mixed with a macromer solution and become suspended at a concentration of 30% w/w. The macromer solution contains 10% diacrylate end-capped pluronic diacrylate, 5% N-isopropyl alcohol, 2.5% EGDMA, 0.5% benzolyl peroxide, 5% PVP, 5% ReoProg®, 5% TAXOL, and 67% $H_2O$. The Au suspension solution is applied as a coating to the surface of the stents with a wet weight of 1000 μg. The coating is heated at 65° C. for 4 minutes to induce a cross-linking reaction. Following the cross-linking reaction, the coating is dried in a vacuum oven at 40° C. for 12 hr. Then the macromer solution (without Au particles) is applied to the surface of the stents by dip-coating with a wet weight of 800 μg. The coating is heated at 65° C. for 4 minutes to induce a cross-linking reaction. Following the cross-linking reaction, the coating is dried in a vacuum oven at 40° C. for 12 hr. The coating is activated by directing a 900-1200 nm wavelength light in the infrared region of the electromagnetic spectrum to the coating.

Example 3

Stents are cleaned with isopropyl alcohol in combination with ultrasonication. Au particles are mixed with a macromer solution and become suspended at a concentration of 30% w/w. A 95:5 molar ratio of dimethyl aminoethylmethacrylate (DMAEMA) and acrylic acid (AAc) has an LCST of about 40° C. The macromer solution contains 10% DMAEMA, 0.5% AAc, 2.5% EGDMA, 0.5% benzolyl peroxide, 5% PVP, 5% ReoPro®, 5% R-7 conjugated heparin, and 71.5% $H_2O$. The Au suspension solution is applied as a coating to the surface of the stents with a wet weight of 1000 μg. The coating is heated at 65° C. for 4 minutes to induce a cross-linking reaction. Following the cross-linking reaction, the coating is dried in a vacuum oven at 40° C. for 12 hr. Then the macromer solution (without Au particles) is applied to the surface of the stents by dip-coating with a wet weight of 800 μg. The coating is heated at 65° C. for 4 minutes to induce a cross-linking reaction. Following the cross-linking reaction, the coating is dried in a vacuum oven at 40° C. for 12 hr. The coating is activated by directing a 900-1200 nm wavelength light in the infrared region of the electromagnetic spectrum to the coating.

Example 4

Stents are cleaned with isopropyl alcohol in combination with ultrasonication. Au particles with different sizes are mixed with a macromer solution and become suspended at a concentration of 30% w/w. The macromer solution contains 15% diacrylate end-capped temperature sensitive polymers with a LCST greater than 40° C., 2.5% EGDMA, 0.5% benzolyl peroxide, 5% PVP, 5% ReoProg®, 5% R-7 conjugated heparin, and 67% $H_2O$. The Au suspension solution is applied as a coating to the surface of the stents with a wet weight of 1000 μg. The coating is heated at 65° C. for 4 minutes to induce a cross-linking reaction. Following the cross-linking reaction, the coating is dried in a vacuum oven at 40° C. for 12 hr. Then the macromer solution (without Au particles) is applied to the surface of the stents by dip-coating with a wet weight of 800 μg. The coating is heated at 65° C. for 4 minutes to induce a cross-linking reaction. Following the cross-linking reaction, the coating is dried in a vacuum oven at 40° C. for 12 hr. The coating is activated by directing a 900-1200 nm wavelength light in the infrared region of the electromagnetic spectrum to the coating.

Example 5

Stents are cleaned with isopropyl alcohol in combination with ultrasonication. Au particles are mixed with a macromer solution and become suspended at a concentration of 30% w/w. A 93:7 molar ratio of DMAEMA and AAc has an LCST of about 42° C. The macromer solution contains 9.6% DMAEMA, 0.9% AAc 2.5% EGDMA, 0.5% benzolyl peroxide, 5% PVP, 5% ReoProg®, 5% R-7 conjugated heparin, and 71.5% $H_2O$. The Au suspension solution is applied as a coating to the surface of the stents with a wet weight of 1000 μg. The coating is heated at 65° C. for 4 minutes to induce a cross-linking reaction. Following the cross-linking reaction, the coating is dried in a vacuum oven at 40° C. for 12 hr. Then the macromer solution (without Au particles) is applied to the surface of the stents by dip-coating with a wet weight of 800 μg. The coating is heated at 65° C. for 4 minutes to induce a cross-linking reaction. Following the cross-linking reaction, the coating is dried in a vacuum oven at 40° C. for 12 hr.

Example 6

Stents are cleaned with isopropyl alcohol in combination with ultrasonication. Au particles (232 nm diameter silica core and 12 nm Au shell thickness) are mixed with a macromer solution and become suspended at a concentration of 30% w/w. A 95:5 molar ratio of NIPAAm and Acryl amide (AAm) has an LCST of about 40° C. The macromer solution contains 9.5% NIPAAm, 0.5% AAm, 2.5% EGDMA, 0.5% benzolyl peroxide, 5% PVP, 5% ReoProg®, 5% R-7 conjugated heparin, and 72% $H_2O$. The Au suspension solution is applied as a coating to the surface of the stents with a wet weight of 1000 μg. The coating is heated at 65° C. for 4 minutes to induce a cross-linking reaction. Following the cross-linking reaction, the coating is dried in a vacuum oven at 40° C. for 12 hr. Then the macromer solution (without Au particles) is applied to the surface of the stents by dip-coating with a wet weight of 800 μg. The coating is heated at 65° C. for 4 minutes to induce a cross-linking reaction. Following the cross-linking reaction, the coating is dried in a vacuum oven at 40° C. for 12 hr.

In another example an elastin-mimetic di-block copolypeptide is cross-linked by the same method as above. The LCST can be adjusted to a range of about 40-43° C. by adjusting the ratio of the hydrophobic and the hydrophilic block. An example of a hydrophobic block is [-Ile-Pro-Gly-Val-Gly-]. An example of a hydrophilic block is [-Val-Pro-Gly-Glu-Gly-]). Examples of cross-linking constituents include disuccinimydil glutarate and disuccinimydil suberate.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

What is claimed is:

1. A stent for delivering a therapeutic substance, comprising:
    a stent body having depots on a surface of the stent body;
    a first material including a therapeutic substance; and
    a second material configured to convert a first type of energy received by the second material from an energy source to a second type of energy, wherein the second type of energy promotes release of the therapeutic substance from the first material, wherein the second material is in the depots of the stent body and wherein the second material is disposed over a surface of the depots.

2. The stent of claim 1, wherein the second material is selected from the group consisting of Au, Au-alloy, Au with a silica core, and ferrimagnetic glass-ceramic.

3. The stent of claim 1, wherein the second type of energy is thermal energy.

4. The stent of claim 1, further comprising a topcoat deposited over at least a portion of the first material.

5. The stent of claim 4, wherein the topcoat includes a polymer.

6. The stent of claim 1, wherein the second material comprises Au particles having a silica nanoparticle core.

7. The stent of claim 6, wherein the silica nanoparticle core has a diameter from 100 to 250 nm.

8. The stent of claim 6, wherein the Au particles include an Au shell having a thickness of 1 to 100 nm.

9. The stent of claim 1, wherein the second material is capable of converting electromagnetic waves with wavelengths between 800 and 1200 nm into thermal energy.

10. The stent of claim 1, wherein the first material includes a temperature-sensitive hydrogel.

11. The stent of claim 10, wherein the temperature-sensitive hydrogel is in thermal communication with the second material.

12. The stent of claim 10, wherein the temperature-sensitive hydrogel is selected from the group consisting of N-isopropylacrylamide, polyoxyethylene-polyoxypropylene block copolymers, poly(acrylic acid) grafted pluronic copolymers, chitosan grafted pluronic copolymer, elastin mimetic polypeptides, and combinations and mixtures thereof.

13. The stent of claim 10, wherein the temperature-sensitive hydrogel has a lower critical solution temperature greater than 37° C.

14. The stent of claim 10, wherein the temperature-sensitive hydrogel is an anionic hydrogel and the therapeutic substance is a cationic substance.

15. The stent of claim 1, wherein the second material is ferrimagnetic glass-ceramic.

16. The stent of claim 1, wherein the second material completely fills at least some of the depots.

17. A stent for delivering a therapeutic substance in a body vessel, comprising a stent body having depots on a surface of the stent body, the stent body carrying:
    a first material including a therapeutic substance;
    a second material configured to convert a first type of energy received by the second material from an energy source to a second type of energy, wherein the second type of energy promotes release of the therapeutic substance from the first material, and wherein the second material is in the depots of the stent body; and
    a third material configured to convert a third type of energy received by the third material from an energy source to a fourth type of energy, wherein the fourth type of energy promotes release of the therapeutic substance from the stent body.

18. The stent of claim 17, wherein the first type of energy and the third type of energy are electromagnetic energy, and wherein the electromagnetic energy of the first energy type has a different wavelength than the third energy type.

19. A stent for delivering a therapeutic substance in a body vessel, comprising:
    a radially expandable stent body;
    a first material including a therapeutic substance; and a second material configured to convert non-cytotoxic electromagnetic waves received by the second material to a first type of energy, wherein the first type of energy promotes the release of the therapeutic substance from the first material, wherein the stent body includes cavities and wherein the second material is deposited in the cavities of the stent body and over the surface of the cavities.

20. The stent of claim 19, wherein the second material is capable of converting electromagnetic waves with wavelengths between 800 and 1200 nm into thermal energy.

21. The stent of claim 19, wherein the second material is selected from the group consisting of Au, Au-alloy, Au with a silica core, and ferrimagnetic glass-ceramic.

22. The stent of claim 19, wherein the first type of energy is thermal energy.

23. The stent of claim 19, further comprising a topcoat deposited over at least a portion of the first material.

24. The stent of claim 23, wherein the topcoat includes a polymer.

25. The stent of claim 19, wherein the second material comprises Au particles having a silica nanoparticle core.

26. The stent of claim 25, wherein the silica nanoparticle core has a diameter from 100 to 250 nm.

27. The stent of claim 25, wherein the Au particles include an Au shell having a thickness of 1 to 100 nm.

28. The stent of claim 19, wherein the first material is includes a temperature-sensitive hydrogel.

29. The stent of claim 28, wherein the temperature-sensitive hydrogel is in thermal communication with the second material.

30. The stent of claim 28, wherein the temperature-sensitive hydrogel is selected from the group consisting of N-isopropylacrylamide, polyoxyethylene-polyoxypropylene block copolymers, poly(acrylic acid) grafted pluronic copolymers, chitosan grafted pluronic copolymer, elastin mimetic polypeptides, and combinations and mixtures thereof.

31. The stent of claim 28, wherein the temperature-sensitive hydrogel has a lower critical solution temperature greater than 37° C.

32. The stent of claim 28, wherein the temperature-sensitive hydrogel is an anionic hydrogel and the therapeutic substance is a cationic substance.

33. The stent of claim 19, wherein the second material is ferrimagnetic glass-ceramic.

34. The stent of claim 19, wherein the second material completely fills at least some of the depots.

35. A stent for delivering a therapeutic substance in a body vessel, comprising:
a radially expandable stent body;
a first material including a therapeutic substance;
a second material configured to convert non-cytotoxic electromagnetic waves received by the second material to a first type of energy, wherein the first type of energy promotes the release of the therapeutic substance from the first material, wherein the stent body includes cavities and wherein the second material is deposited in the cavities of the stent body; and
a third material configured to convert a second type of energy received by the third material to a third type of energy, wherein the third type of energy promotes release of the therapeutic substance from the stent body.

36. The stent of claim 35, wherein the second type of energy is electromagnetic energy, and wherein the electromagnetic waves received by the second material have a different wavelength than the second energy type.

37. A stent for delivering a therapeutic substance in a body vessel, comprising a stent body having depots on a surface of the stent body, the stent body carrying:
a first material including a therapeutic substance;
a second material configured to convert a first type of energy received by the second material from an energy source to a second type of energy, wherein the second type of energy promotes release of the therapeutic substance from the first material, and wherein the second material is in the depots of the stent body; and
a second therapeutic substance and a third material configured to convert a third type of energy received by the third material from an energy source to a fourth type of energy, wherein the fourth type of energy promotes release of the second therapeutic substance from the stent body.

38. The stent of claim 37, wherein the first type of energy and the third type of energy are electromagnetic energy, and wherein the electromagnetic energy of the first energy type has a different wavelength than the third energy type.

39. The stent of claim 37, wherein the second therapeutic substance is included in the first material or in a fourth material carried by the stent body.

40. A stent for delivering a therapeutic substance in a body vessel, comprising:
a radially expandable stent body;
a first material including a therapeutic substance;
a second material configured to convert non-cytotoxic electromagnetic waves received by the second material to a first type of energy, wherein the first type of energy promotes the release of the therapeutic substance from the first material, wherein the stent body includes cavities and wherein the second material is deposited in the cavities of the stent body; and
a second therapeutic substance and a third material configured to convert a second type of energy received by the third material to a third type of energy, wherein the third type of energy promotes release of the second therapeutic substance from the stent body.

41. The stent of claim 40, wherein the second type of energy is electromagnetic energy and wherein the electromagnetic waves received by the second material have a different wavelength than the second type of energy.

42. The stent of claim 40, wherein the second therapeutic substance is included in the first material or in a fourth material carried by the stent body.

43. A stent for delivering a therapeutic substance, comprising:
a stent body having depots on a surface of the stent body;
a first material including a therapeutic substance; and
a second material configured to convert a first type of energy received by the second material from an energy source to a second type of energy, wherein the second type of energy promotes release of the therapeutic substance from the first material, and wherein the second material is in the depots of the stent body and the second material is different than surface material of the depots.

44. The stent of claim 43, wherein the second material is selected from the group consisting of Au, Au-alloy, Au with a silica core, and ferrimagnetic glass-ceramic.

45. The stent of claim 43, wherein the second type of energy is thermal energy.

46. The stent of claim 43, further comprising a coating deposited over at least a portion of the first material.

47. The stent of claim 43, wherein the second material comprises Au particles having a silica nanoparticle core.

48. The stent of claim 47, wherein the silica nanoparticle core has a diameter from 100 to 250 nm.

49. The stent of claim 47, wherein the Au particles include an Au shell having a thickness of 1 to 100 nm.

50. The stent of claim 43, wherein the second material is capable of converting electromagnetic waves with wavelengths between 800 and 1200 nm into thermal energy.

51. The stent of claim 43, wherein the first material includes a temperature-sensitive hydrogel.

52. The stent of claim 51, wherein the temperature-sensitive hydrogel is in thermal communication with the second material.

53. The stent of claim 51, wherein the temperature-sensitive hydrogel is selected from the group consisting of N-isopropylacrylamide, polyoxyethylene-polyoxypropylene block copolymers, poly(acrylic acid) grafted pluronic copolymers, chitosan grafted pluronic copolymer, elastin mimetic polypeptides, and combinations and mixtures thereof.

54. The stent of claim 43, wherein the depots are at least partially filled with the second material.

* * * * *